United States Patent [19]

Wright, Jr. et al.

[11] 4,325,955

[45] Apr. 20, 1982

[54] SUBSTITUTED 3-BENZHYDRYLTHIAZOLO(3,2-a)PYRIMIDINES

[75] Inventors: William B. Wright, Jr., Woodcliff Lake; Andrew S. Tomcufcik, Old Tappan, both of N.J.; Joseph W. Marisco, Jr., Pearl River, N.Y.

[73] Assignee: American Cyanamid Company, Stamford, Conn.

[21] Appl. No.: 246,346

[22] Filed: Mar. 23, 1981

[51] Int. Cl.$^3$ ............... A61K 31/415; A61K 31/425; C07D 513/04
[52] U.S. Cl. .................................. 424/251; 544/278; 260/245.7; 424/270
[58] Field of Search ................... 544/278; 424/251

[56] References Cited

U.S. PATENT DOCUMENTS

| | | | |
|---|---|---|---|
| 3,671,526 | 6/1972 | Manning | 544/278 |
| 3,686,173 | 8/1972 | Houlihan et al. | 424/251 |
| 4,110,451 | 8/1978 | Moser et al. | 424/251 |

OTHER PUBLICATIONS

Houlihan, et al, Chem. Abst. 72:111502w.

*Primary Examiner*—Anton H. Sutto
*Assistant Examiner*—Sharon A. Gibson
*Attorney, Agent, or Firm*—Edward A. Conroy, Jr.

[57] ABSTRACT

This disclosure describes substituted 3-benzhydrylthiazolo(3,2-a)pyridines which are useful as diuretic agents.

11 Claims, No Drawings

SUBSTITUTED 3-BENZHYDRYLTHIAZOLO(3,2-a)PYRIMIDINES

BRIEF SUMMARY OF THE INVENTION

This invention relates to new organic compounds and, more particularly, is concerned with novel substituted 3-benzhydrylthiazolo[3,2-a][1,3]diazacyclenes which may be represented by the following structural formula:

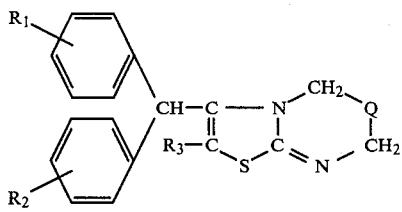

wherein $R_1$ is hydrogen, fluoro, chloro, bromo or alkyl having up to 3 carbon atoms; $R_2$ is hydrogen, fluoro, chloro, bromo or alkyl having up to 3 carbon atoms; $R_3$ is hydrogen or alkyl having up to 3 carbon atoms; and Q is a divalent moiety of the formulae:

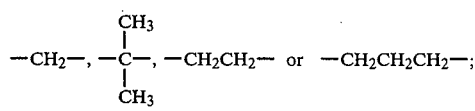

as well as the pharmaceutically acceptable acid-addition salts thereof. The invention is also concerned with pharmaceutical compositions comprising these new compounds as well as methods for inducing diuresis employing these new compounds and, further, to methods for their preparation.

DETAILED DESCRIPTION OF THE INVENTION

The novel free bases of the present invention are obtainable as either white to light tan crystalline materials having characteristic melting points or as oils having characteristic absorption spectra. The free bases are, in general, relatively insoluble in water but soluble in most organic solvents such as lower alkanols, benzene, acetone, chloroform, etc. The organic bases of this invention form acid-addition salts with a variety of pharmacologically acceptable organic and inorganic salt-forming reagents. Thus, acid-addition salts, formed by admixture of the organic free base with an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. For purposes of this invention, the free bases are equivalent to their acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention may be readily prepared in accordance with the following reaction scheme:

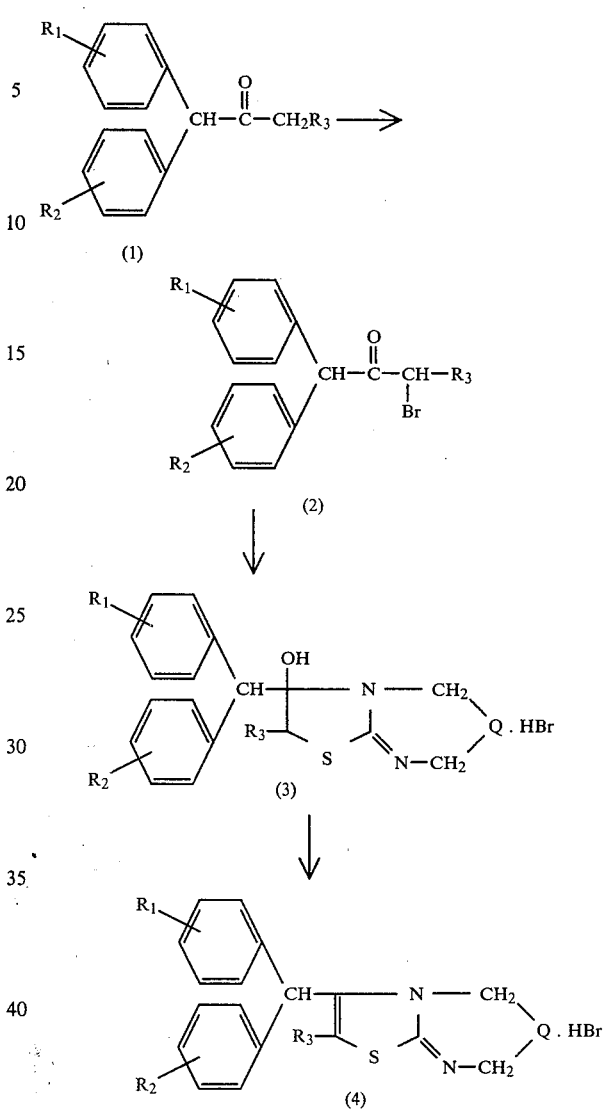

wherein $R_1$, $R_2$, $R_3$ and Q are as hereinbefore defined. In accordance with the above reaction scheme, an appropriately substituted 1,1-diaryl-2-alkanone (1) is dissolved in glacial acetic acid and treated with about one equivalent of bromine at 60°–70° C. whereby the corresponding 1,1-diaryl-3-bromo-2-alkanone (2) is obtained. Treatment of (2) with tetrahydropyrimidine-2(1H)-thione, tetrahydro-5,5-dimethylpyrimidine-2(1H)-thione, hexahydro-1,3-diazepin-2(2H)-thione or hexahydro-1,3-diazocin-2(1H)-thione in acetone as solvent at the reflux temperature thereof provides the corresponding 3-benzhydrylthiazolo[3,2-a][1,3]-dizacyclan-3-ol (3). Heating the diazacyclanol (3) above its decomposition point, usually 160°–220° C., for from about 5 to about 30 minutes provides the dehydrated product (4). Alternatively, the diazacyclanol (3) may be boiled in a solvent such as ethanol, butanol or dioxane until dehydration has occurred. Addition of an acid such as hydrochloric or hydrobromic promotes the reaction.

In general terms, the process of step one may be carried out in glacial acetic acid or an equivalent at 50°–80° C. for 30 minutes to 4 hours. Suitable solvents for the second step include acetone, methylethylketone, chloroform, benzene, toluene and the like and the reaction may range from 25°–60° C. for one to 72 hours. Procedures for the preparation of the 1,1-diaryl-2-alkanones (1) are well known and may be found in such references as: M. J. Hatch and D. J. Cram, J.A.C.S. 75, 38 (1953); E. J. Cragoe, Jr., A. M. Pietruszkiewicz and C. M. Robb, J. Org. Chem. 23, 971 (1958); E. M. Schultz, U.S. Pat. No. 2,703,329. It is also possible to prepare the 1,1-diaryl-3-bromo-2-alkanone derivatives (2) by other methods, for example, the Arndt-Eistert synthesis of an acid with diazomethane and hydrobromic acid [G. W. Wheland, Advanced Organic Chemistry, John Wiley and Sons, Inc., 2nd Edition, p. 462 (1948)].

The new compounds of the present invention possess diuretic activity in warm-blooded animals as established when tested by the method of P. S. Chan and D. Poorvin, Clinical and Experimental Hypertension, 1 (6), 817–830 (1979), "Sequential Method for Combined Screening Antihypertensive and Diuretic Agents in the Same Spontaneously Hypertensive Rat". Basically this test uses male, 8 week old, spontaneously hypertensive rats of the Okamoto strain weighing about 300 g. One rat is dosed by gavage with the test compound at 100 mg./kg. of body weight with 0.9% sodium chloride loading at 25 ml./kg. of body weight at zero hour. The test compound is suspended in 2% preboiled starch at 50 mg./ml. The rat is placed in a metabolism cage and the 0–5 hour urine is collected. The urinary sodium, potassium and chloride content are determined by the Technicon Autoanalyzer; method N-20 for sodium and potassium and method N-5b for chloride. At the end of the fifth hour, the rat is placed in a regular animal cage and provided with water ad libitum. A second identical dose of the test compound is given by gavage, without sodium chloride loading, at the 24th hour. Four hours later, the rat is restrained in a supine position with elastic tapes. The femoral area is locally anesthetized by subcutaneous infiltration of 2% lidocaine. The iliac artery is isolated and punctured with a 26 gauge thin wall needle which is connected to a Statham P23Db pressure transducer-Beckman Dynograph recorder system for monitoring blood pressure. The blood pressure is recorded for 15 minutes or until it is stabilized. Based on the data obtained and using the three-stage "sequential probability ratio test", statistical method, the criteria for determining if a test compound is considered active are as follows:

Test I: If the mean arterial blood pressure (MABP) is $\leq 116$ and/or the urinary sodium is $\geq 1.21$ mEq, the compound is active. If the MABP is between 117–146 and/or the urinary sodium is between 1.21–0.93, a second rat is tested.

Test II: If the average MABP of the two rats is $< 122$ and/or the average urinary sodium of the two rats is $> 1.16$ mEq, the compound is considered active. If the MABP is between 123–137 and/or the average urinary sodium is between 1.16–1.01, a third rat is tested.

Test III: If the average MABP of the three rats is $\leq 128$ and/or the average urinary sodium is $\geq 1.10$, the compound is active.

The results of this test on representative compounds of the present invention appear in Table I.

TABLE I

| Compound | Urinary Values in mEq/5 hr. | | |
|---|---|---|---|
| | Vol. (ml.) | Na+ | K+ |
| 3-[o-Fluoro-α-(p-fluorophenyl)benyl]-6,7-dihydro-5H-thiazolo[3,2-a]pyrimidine hydrobromide | 21.5 | 2.55 | 0.59 |
| 3-(p-Methyl-α-phenylbenzyl)-6,7-dihydro-5H-thiazolo[3,2-a]pyrimidine hydrobromide | 17.5 | 1.68 | 0.63 |
| 3-(p-Fluoro-α-phenylbenzyl)-6,7-dihydro-5H-thiazolo[3,2-a]pyrimidine hydrobromide | 19.0 | 2.02 | 0.49 |
| 3-[p-Chloro-α-(p-fluorophenyl)benzyl]-6,7-dihydro-5H-thiazolo[3,2-a]pyrimidine hydrobromide | 11.5 | 1.50 | 0.83 |
| 3-[Bis-(p-fluorophenyl)methyl]-6,7-dihydro-5H-thiazolo[3,2-a]pyrimidine hydrobromide | 17.5 | 2.19 | 0.76 |
| 3-(p-Fluoro-α-phenylbenzyl)-6,7-dihydro-6,6-dimethyl-5H-thiazolo[3,2-a]pyrimidine hydrobromide | 14.8 | 1.50 | 0.48 |
| 3-(p-Fluoro-α-m-tolylbenzyl)-6,7-dihydro-6,6-dimethyl-5H-thiazolo[3,2-a]pyrimidine hydrobromide | 15.5 | 1.75 | 0.54 |
| 3-[o-Chloro-α-(p-fluorophenyl)benzyl]-6,7-dihydro-6,6-dimethyl-5H-thiazolo[3,2-a]pyrimidine hydrobromide | 14.3 | 1.47 | 0.55 |
| 3-[p-Chloro-α-(p-fluorophenyl)benzyl]-6,7-dihydro-6,6-dimethyl-5H-thiazolo[3,2-a]pyrimidine hydrobromide | 14.2 | 1.74 | 0.66 |
| 3-[o-Fluoro-α-(p-fluorophenyl)benzyl]-6,7-dihydro-6,6-dimethyl-5H-thiazolo[3,2-a]pyrimidine hydrobromide | 14.0 | 1.40 | 0.55 |
| 3-[m-Fluoro-α-(p-fluorophenyl)benzyl]-6,7-dihydro-6,6-dimethyl-5H-thiazolo[3,2-a]pyrimidine hydrobromide | 16.8 | 1.73 | 0.61 |
| 3-[Bis-(p-fluorophenyl)methyl]-6,7-dihydro-6,6-dimethyl-5H-thiazolo[3,2-a]pyrimidine hydrobromide | 17.5 | 1.73 | 0.53 |
| 3-[p-Chloro-α-(p-fluorophenyl)benzyl]-5,6,7,8-tetrahydrothiazolo[3,2-a][1,3]diazepine hydrobromide | 11.0 | 1.51 | 0.71 |
| 3-(p-Fluoro-α-phenylbenzyl)-5,6,7,8-tetrahydrothiazolo[3,2-a][1,3]diazepine hydrobromide | 18.5 | 2.41 | 0.91 |
| 3-[o-Chloro-α-(p-fluorophenyl)benzyl]-5,6,7,8-tetrahydrothiazolo[3,2-a][1,3]diazepine hydrobromide | 19.0 | 1.92 | 0.63 |
| 3-[Bis-(p-fluorophenyl)methyl]-5,6,7,8-tetrahydrothiazolo[3,2-a][1,3]diazepine hydrobromide | 24.3 | 2.98 | 0.72 |

The novel compounds of the present invention have thus been shown to be valuable diuretic agents of low toxicity when administered orally. The amount of a single dose or of a daily dose will vary but should be such as to give a proportionate dosage of from about 5 mg. to about 100 mg. per day for a subject of about 70 kg. body weight. The dosage regimen may be adjusted to provide the optimum therapeutic response, for example, doses of 1.0–25 mg. may be administered on a four times per day regimen, or the dose may be proportionately increased as indicated by the exigencies of the therapeutic situation.

The compounds of the present invention may be administered as active components of compositions in unit dosage form such as tablets, pills, capsules, powders, granules, oral solutions or suspensions and the like. For preparing solid compositions such as tablets, the active compound is mixed with conventional tableting ingredients such as starch, lactose, sucrose, sorbitol, talc, stearic acid, magnesium stearate, dicalcium phosphate, gums and functionally similar materials as pharmaceutical diluents or carriers. The tablets or pills can be laminated or otherwise compounded to provide a dosage form affording the advantage of prolonged or delayed action, or predetermined successive action of the enclosed medication. For example, the tablet or pill can comprise an inner dosage and an outer dosage component, the latter being in the form of an envelop over the former. The two components can be separated by an enteric layer which serves to resist disintegration in the stomach and permits the inner component to pass intact into the duodenum or to be delayed in response. A variety of materials can be used for such enteric layers or coatings, such materials including a number of polymeric acids or mixtures of polymeric acids with such materials as shellac, shellac and and cetyl alcohol, cellulose acetate, and the like. A particularly advantageous enteric coating comprises a styrene maleic acid copolymer together with known materials contributing to the enteric properties of the coating.

The liquid forms in which the compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use.

A preferred embodiment of the present invention may be represented by structural formula (I) but wherein $R_1$ is hydrogen, methyl, fluoro, chloro or bromo; $R_2$ is hydrogen, methyl, fluoro, chloro or bromo; $R_3$ is hydrogen or methyl; and Q is a divalent moiety of the formula:

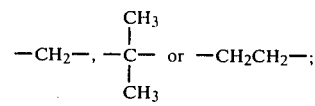

as well as the pharmacologically acceptable acid-addition salts thereof.

The invention will be described in greater detail in conjunction with the following specific examples.

EXAMPLE 1

1-(m-Fluorophenyl)-1-(p-fluorophenyl)-2-propanone

A solution of 16.5 g. of m-fluorophenyl-2-propanone [Z. Eckstein and J. Plenkiewicz, Rocznik, Chem., 37, 907 (1963)] in 70 ml. of p-fluorobenzene is cooled and stirred as 5.5 ml. of bromine are added dropwise. Argon gas is bubbled through the mixture for one hour. The solution is then added dropwise to a mixture of 29.6 g. of aluminum chloride and 70 ml. of p-fluorobenzene, stirred at 80°–90° C. Stirring is continued at this temperature for one hour then the mixture is poured into ice and 45 ml. of concentrated hydrochloric acid. Toluene is added, the organic layer is separated, washed with dilute sodium hydroxide and then water and distilled, giving the desired product as a liquid, b.p. 106°–112° C. (0.15 mm.).

When the appropriate 1-aryl-2-alkanone is reacted with a benzene derivative (as reagent and solvent) by the procedure described in Example 1, the intermediates of Examples 2–20 (listed in tabular form) are derived.

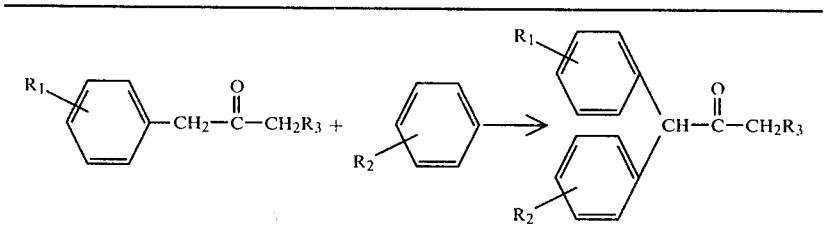

| | 1-Aryl-2-alkanone | | Benzene Derivative | | |
|---|---|---|---|---|---|
| Ex. | $R_1$ | $R_3$ | $R_2$ | Intermediate | B.P. °C./mm. |
| 2 | H | H | p-Cl | 1-(p-chlorophenyl)-1-phenyl-2-propanone | 150–156/0.4 |
| 3 | H | H | p-F | 1-(p-fluorophenyl)-1-phenyl-2-propanone | 142–146/<1 |
| 4 | H | H | p-Br | 1-(p-bromophenyl)-1-phenyl-2-propanone | 134–138/0.15 |
| 5 | H | H | p-CH₃ | 1-phenyl-1-p-tolyl-2-propanone | 140–144/<1 |
| 6 | m-Cl | H | p-CH₃ | 1-(m-chlorophenyl)-1-p-tolyl-2-propanone | 130–136/0.2 |
| 7 | o-F | H | p-CH₃ | 1-(o-fluorophenyl)-1-p-tolyl-2-propanone | 130–136/0.2 |
| 8 | m-F | H | p-CH₃ | 1-(m-fluorophenyl)-1-p-tolyl-2-propanone | 111–120/0.2 |
| 9 | p-CH₃ | H | p-F | 1-(p-fluorophenyl)-1-p-tolyl-2-propanone | 116–122/0.15 |
| 10 | m-CH₃ | H | p-CH₃ | 1-m-tolyl-1-p-tolyl-2-propanone | 126–132/0.2 |
| 11 | p-Cl | H | p-Cl | 1,1-bis(p-chlorophenyl)-2-propanone | 170–178/<1 |

-continued

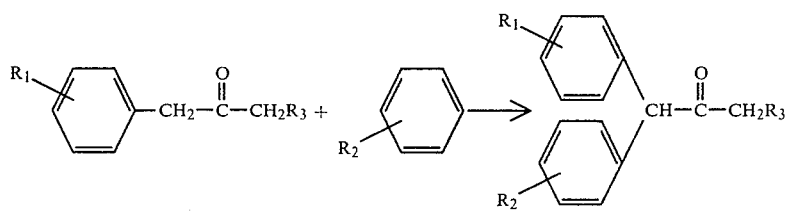

| Ex. | 1-Aryl-2-alkanone R₁ | R₃ | Benzene Derivative R₂ | Intermediate | B.P. °C./mm. |
|---|---|---|---|---|---|
| 12 | p-Cl | H | p-F | 1-(p-chlorophenyl)-1-(p-fluorophenyl)-2-propanone | 130–136/0.2 |
| 13 | o-Cl | H | p-F | 1-(o-chlorophenyl)-1-(p-fluorophenyl)-2-propanone | 114–120/0.15 |
| 14 | o-F | H | p-F | 1-(o-fluorophenyl)-1-(p-fluorophenyl)-2-propanone | 100–106/0.15 |
| 15 | m-F | H | p-F | 1-(m-fluorophenyl)-1-(p-fluorophenyl)-2-propanone | 106–112/0.15 |
| 16 | p-F | H | p-F | 1,1-bis(p-fluorophenyl)-2-propanone | 120–126/0.2 |
| 17 | m-CH₃ | H | p-F | 1-(p-fluorophenyl)-1-m-tolyl-2-propanone | 116–122/0.15 |
| 18 | H | CH₃ | p-Cl | 1-(p-chlorophenyl)-1-phenyl-2-butanone | 155–160/<1 |
| 19 | H | CH₃ | p-F | 1-(p-fluorophenyl)-1-phenyl-2-butanone | 142–146/<1 |
| 20 | p-F | CH₃ | p-F | 1,1-bis(p-fluorophenyl)-2-butanone | 128–132/0.4 |

EXAMPLE 21

3-Diphenylmethyl-2,3,6,7-tetrahydro-5H-thiazolo[3,2-a]pyrimidin-3-ol hydrobromide A solution of 2.1 g. of 1,1-diphenyl-2-propanone in 25 ml. of acetic acid is heated to 60°–70° C. and 0.5 ml. of bromine in 4 ml. of acetic acid is added dropwise. The reaction mixture is held at 60°–70° C. for one hour and then poured into ice. Toluene is added. The toluene layer is separated, washed with water, dried over magnesium sulfate and concentrated, giving 1-bromo-3,3-diphenyl-2-propanone.

The 1-bromo-3,3-diphenyl-2-propanone is dissolved in 15 ml. of acetone and added to a boiling mixture of 0.80 g. of tetrahydro-2-pyrimidinethione in 70 ml. of acetone. This mixture is allowed to stand for 48 hours and the resulting solid is collected by filtration, giving the desired product, m.p. 196°–198° C.

When the procedure of Example 21 is carried out using, instead of 1,1-diphenyl-2-propanone, the intermediate diarylketones of Examples 1–20, the final products of Examples 22–39 (listed in tabular form) are derived.

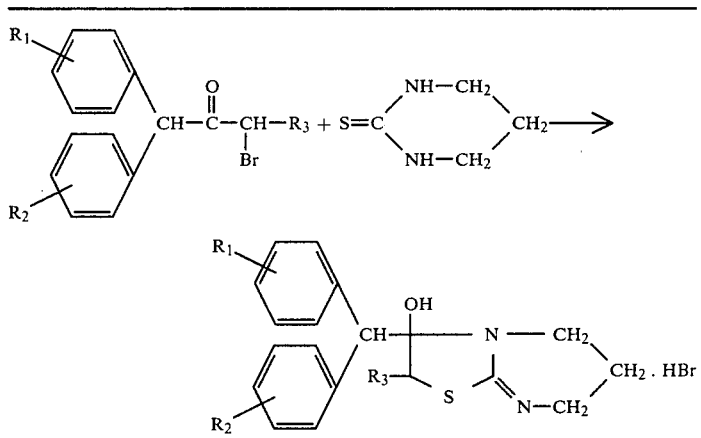

| Ex. | Intermediate Ex. No. | Product | M.P. °C. |
|---|---|---|---|
| 22 | 2 | 3-(p-chloro-α-phenylbenzyl)-2,3,6,7-tetrahydro-5H-thiazolo[3,2-a]pyrimidin-3-ol hydrobromide | 177–179 |
| 23 | 3 | 3-(p-fluoro-α-phenylbenzyl)-2,3,6,7-tetrahydro-5H-thiazolo[3,2-a]pyrimidin-3-ol hydrobromide | 174–176 |
| 24 | 4 | 3-(p-bromo-α-phenylbenzyl)-2,3,6,7-tetrahydro-5H-thiazolo[3,2-a]pyrimidin-3-ol hydrobromide | 163–166 |
| 25 | 5 | 3-(p-methyl-α-phenylbenzyl)-2,3,6,7-tetrahydro-5H-thiazolo[3,2-a]pyrimidin-3-ol hydrobromide | 163–165 |
| 26 | 6 | 3-(m-chloro-α-p-tolylbenzyl)-2,3,6,7-tetrahydro-5H-thiazolo[3,2-a]pyrimidin-3-ol hydrobromide | 184–186 |
| 27 | 7 | 3-(o-fluoro-α-p-tolylbenzyl)-2,3,6,7-tetrahydro- | 188–190 |

-continued

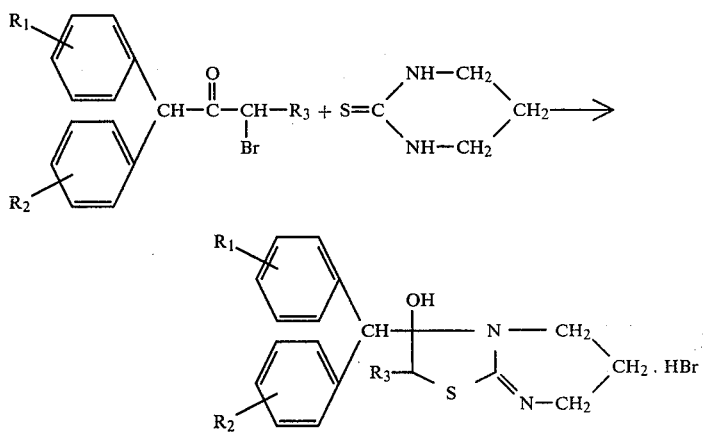

| Ex. | Intermediate Ex. No. | Product | M.P. °C. |
|---|---|---|---|
| | | 5H-thiazolo[3,2-a]pyrimidin-3-ol hydrobromide | |
| 28 | 8 | 3-(m-fluoro-α-p-tolylbenzyl)-2,3,6,7-tetrahydro-5H-thiazolo[3,2-a]pyrimidin-3-ol hydrobromide | 138–140 |
| 29 | 9 | 3-(p-fluoro-α-p-tolylbenzyl)-2,3,6,7-tetrahydro-5H-thiazolo[3,2-a]pyrimidin-3-ol hydrobromide | 135–137 |
| 30 | 10 | 3-(m-methyl-α-p-tolylbenzyl)-2,3,6,7-tetrahydro-5H-thiazolo[3,2-a]pyrimidin-3-ol hydrobromide | 173–175 |
| 31 | 11 | 3-[bis(p-chlorophenyl)methyl-2,3,6,7-tetrahydro-5H-thiazolo[3,2-a]pyrimidin-3-ol hydrobromide | 131–133 |
| 32 | 12 | 3-[p-chloro-α-(p-fluorophenyl)benzyl]-2,3,6,7-tetrahydro-5H-thiazolo[3,2-a]pyrimidin-3-ol hydrobromide | 144–146 |
| 33 | 13 | 3-[o-chloro-α-(p-fluorophenyl)benzyl]-2,3,6,7-tetrahydro-5H-thiazolo[3,2-a]pyrimidin-3-ol hydrobromide | 184–186 |
| 34 | 14 | 3-[o-fluoro-α-(p-fluorophenyl)benzyl]-2,3,6,7-tetrahydro-5H-thiazolo[3,2-a]pyrimidin-3-ol hydrobromide | 190–192 |
| 35 | 15 | 3-[m-fluoro-α-(p-fluorophenyl)benzyl]-2,3,6,7-tetrahydro-5H-thiazolo[3,2-a]pyrimidin-3-ol hydrobromide | 154–156 |
| 36 | 16 | 3-[bis(p-fluorophenyl)methyl]-2,3,6,7-tetrahydro-5H-thiazolo[3,2-a]pyrimidin-3-ol hydrobromide | 172–174 |
| 37 | 18 | 3-(p-chloro-α-phenylbenzyl)-2,3,6,7-tetrahydro-2-methyl-5H-thiazolo[3,2-a]pyrimidin-3-ol hydrobromide | 176–178 |
| 38 | 19 | 3-(p-fluoro-α-phenylbenzyl)-2,3,6,7-tetrahydro-2-methyl-5H-thiazolo[3,2-a]pyrimidin-3-ol hydrobromide | 213–215 |
| 39 | 20 | 3-[bis(p-fluorophenyl)methyl]-2,3,6,7-tetrahydro-2-methyl-5H-thiazolo[3,2-a]pyrimidin-3-ol hydrobromide | 183–185 |

EXAMPLE 40

3-[o-Fluoro-α-(p-fluorophenyl)benzyl]-6,7-dihydro-5H-thiazolo[3,2-a]pyrimidine hydrobromide A test tube containing 1.0 g. of 3-[o-fluoro-α-(p-fluorophenyl)benzyl]-2,3,6,7-tetrahydro-5H-thiazolo[3,2-a]pyrimidine-3-ol hydrobromide is immersed in an oil bath at 215° C. for 20 minutes. The compound decomposes, becomes liquid and then rehardens. A 5 ml. portion of acetone is added and the mixture is stirred and filtered. The crystalline product is washed with acetone and dried in vacuo, giving the desired product, m.p. 291°–293° C.

When the procedure of Example 40 is carried out using, instead of 3-[o-fluoro-α-(p-fluorophenyl)benzyl]-2,3,6,7-tetrahydro-5H-thiazolo[3,2-a]pyrimidine-3-ol hydrobromide, the compounds of Examples 23–25, 27, 29, 32, 33, 35, 36 and 39, the final products of Examples 41–50 (listed in tabular form) are derived.

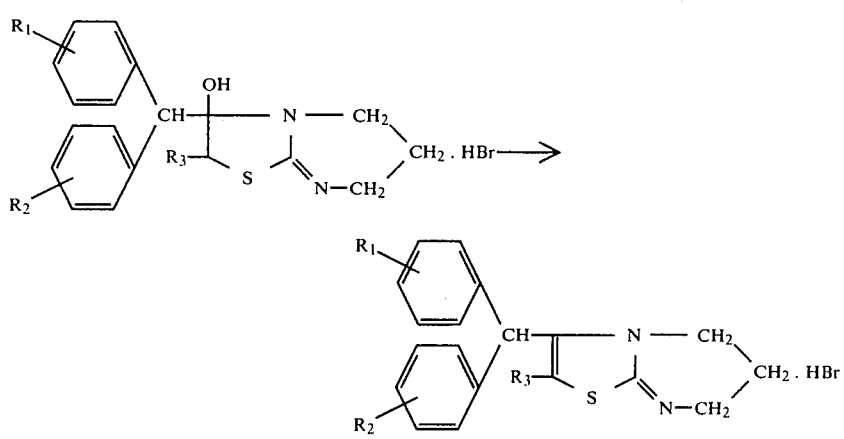

| Ex. | Starting Material Ex. No. | Product | Reaction Conditions Minutes | °C. | M.P. °C. |
|---|---|---|---|---|---|
| 41 | 25 | 3-(p-methyl-α-phenylbenzyl)-6,7-dihydro-5H-thiazolo[3,2-a]pyrimidine hydrobromide | 30 | 190 | 278–280 |
| 42 | 23 | 3-(p-fluoro-α-phenylbenzyl)-6,7-dihydro-5H-thiazolo[3,2-a]pyrimidine hydrobromide | 30 | 200 | 255–257 |
| 43 | 24 | 3-(p-bromo-α-phenylbenzyl)-6,7-dihydro-5H-thiazolo[3,2-a]pyrimidine hydrobromide | 20 | 190 | 285–288 |
| 44 | 27 | 3-(o-fluoro-α-p-tolylbenzyl)-6,7-dihydro-5H-thiazolo[3,2-a]pyrimidine hydrobromide | 20 | 195 | 248–250 |
| 45 | 29 | 3-(p-fluoro-α-p-tolylbenzyl)-6,7-dihydro-5H-thiazolo[3,2-a]pyrimidine hydrobromide | 25 | 170–185 | 244–246 |
| 46 | 33 | 3-[o-chloro-α-(p-fluorophenyl)benzyl]-6,7-dihydro-5H-thiazolo[3,2-a]pyrimidine hydrobromide | 30 | 200 | 275–278 |
| 47 | 32 | 3-[p-chloro-α-(p-fluorophenyl)benzyl]-6,7-dihydro-5H-thiazolo[3,2-a]pyrimidine hydrobromide | 20 | 170 | 240–243 |
| 48 | 35 | 3-(m-fluoro-α-(p-fluorophenyl)benzyl]-6,7-dihydro-5H-thiazolo[3,2-a]pyrimidine hydrobromide | 20 | 185–190 | 263–265 |
| 49 | 36 | 3-[bis(p-fluorophenyl)methyl]-6,7-dihydro-5H-thiazolo[3,2-a]pyrimidine hydrobromide | 20 | 200 | 164–170 |
| 50 | 39 | 3-[bis(p-fluorophenyl)methyl]-6,7-dihydro-2-methyl-5H-thiazolo[3,2-a]pyrimidine hydrobromide | 20 | 200 | 244–146 |

EXAMPLE 51

3-Diphenylmethyl-2,3,6,7-tetrahydro-6,6-dimethyl-5H-thiazolo[3,2-a]pyrimidin-3-ol hydrobromide A 2.1 g. portion of 1,1-diphenyl-2-propanone is converted to 1-bromo-3,3-diphenyl-2-propanone as described in Example 21. This 1-bromo-3,3-diphenyl-2-propanone is dissolved in 15 ml. of acetone and added to a boiling mixture of 1.0 g. of tetrahydro-5,5-dimethyl-2(H)-pyrimidinethione in 50 ml. of acetone. The mixture is allowed to stand at room temperature for 24 hours and the resulting solid is collected by filtration, giving the desired product, m.p. 259°–261° C.

When the procedure of Example 51 is carried out using, instead of 1,1-diphenyl-2-propanone, the intermediate diarylketones of Examples 1–20, the final products of Examples 52–67 (listed in tabular forms) are derived.

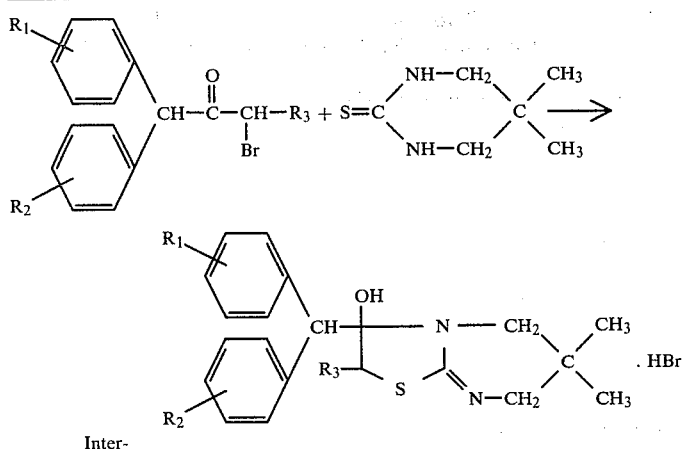

| Ex. | Intermediate Ex. No. | Product | M.P. °C. |
|---|---|---|---|
| 52 | 2 | 3-(p-chloro-α-phenylbenzyl)-2,3,6,7-tetrahydro-6,6-dimethyl-5H-thiazolo[3,2-a]pyrimidin-3-ol hydrobromide | ca 180 |
| 53 | 3 | 3-(p-fluoro-α-phenylbenzyl)-2,3,6,7-tetrahydro-6,6-dimethyl-5H-thiazolo[3,2-a]pyrimidine-3-ol hydrobromide | ca 200 |
| 54 | 4 | 3-(p-bromo-α-phenylbenzyl)-2,3,6,7-tetrahydro-6,6-dimethyl-5H-thiazolo[3,2-a]pyrimidin-3-ol hydrobromide | 180 |
| 55 | 5 | 3-(p-methyl-α-phenylbenzyl)-2,3,6,7-tetrahydro-6,6-dimethyl-5H-thiazolo[3,2-a]pyrimidin-3-ol hydrobromide | 169–171 |
| 56 | 6 | 3-(m-chloro-α-p-tolylbenzyl)-2,3,6,7-tetrahydro-6,6-dimethyl-5H-thiazolo[3,2-a]pyrimidin-3-ol hydrobromide | ca 200 |
| 57 | 7 | 3-(o-fluoro-α-p-tolylbenzyl)-2,3,6,7-tetrahydro-6,6-dimethyl-5H-thiazolo[3,2-a]pyrimidin-3-ol hydrobromide | 170–172 |
| 58 | 9 | 3-(p-fluoro-α-p-tolylbenzyl)-2,3,6,7-tetrahydro-6,6-dimethyl-5H-thiazolo[3,2-a]pyrimidin-3-ol hydrobromide | <200 |
| 59 | 12 | 3-[p-chloro-α-(p-fluorophenyl)benzyl]-2,3,6,7-tetrahydro-6,6-dimethyl-5H-thiazolo[3,2-a]-pyrimidin-3-ol hydrobromide | 192–194 |
| 60 | 13 | 3-]o-chloro-α-(p-fluorophenyl)benzyl]-2,3,6,7-tetrahydro-6,6-dimethyl-5H-thiazolo[3,2-a]-pyrimidin-3-ol hydrobromide | 205 |
| 61 | 14 | 3-[o-fluoro-α-(p-fluorophenyl)benzyl]-2,3,6,7-tetrahydro-6,6-dimethyl-5H-thiazolo[3,2-a]-pyrimidin-3-ol hydrobromide | ca 220 |
| 62 | 15 | 3-[m-fluoro-α-(p-fluorophenyl)benzyl]-2,3,6,7-tetrahydro-6,6-dimethyl-5H-thiazolo[3,2-a]-pyrimidin-3-ol hydrobromide | 203 |
| 63 | 16 | 3-[bis(p-fluorophenyl)methyl]-2,3,6,7-tetrahydro-6,6-dimethyl-5H-thiazolo[3,2-a]pyrimidin-3-ol hydrobromide | 198–200 |
| 64 | 17 | 3-(p-fluoro-α-m-tolylbenzyl)-2,3,6,7-tetrahydro-6,6-dimethyl-5H-thiazolo[3,2-a]pyrimidin-3-ol hydrobromide | ca 200 |
| 65 | 18 | 3-(p-chloro-α-phenylbenzyl)-6,7-dihydro-2,6,6-trimethyl-5H-thiazolo[3,2-a]pyrimidin-3-ol hydrobromide | 166–168 |
| 66 | 19 | 3-(p-fluoro-α-phenylbenzyl)-6,7-dihydro-2,6,6-trimethyl-5H-thiazolo[3,2-a]pyrimidin-3-ol hydrobromide | 175–177 |
| 67 | 20 | 3-[bis(p-fluorophenyl)methyl]-6,7-dihydro-2,6,6-trimethyl-5H-thiazolo[3,2-a]pyrimidin-3-ol hydrobromide | 192–193 |

EXAMPLE 68

3-(p-Fluoro-α-phenylbenzyl)-6,7-dihydro-6,6-dimethyl-5-H-thiazolo[3,2-a]pyrimidine hydrobromide A 2.0 g. portion of 3-(p-fluoro-α-phenylbenzyl)-2,3,6,7-tetrahydro-6,6-dimethyl-5-H-thiazolo[3,2-a]pyrimidin-3-ol hydrobromide is placed in a small Erlenmeyer flask and immersed in an oil bath at 200° C. for 20 minutes. The flask is removed from the bath and the product is triturated with acetone and then filtered. The crystalline product is washed with acetone and dried in vacuo, giving the desired product, m.p. 257°–259° C.

When the procedure of Example 68 is carried out using, instead of 3-(p-fluoro-α-phenylbenzyl)-2,3,6,7- tetrahydro-6,6-dimethyl-5H-thiazolo[3,2-a]pyrimidin-3-ol hydrobromide, the compounds of Examples 51, 52, 54–64 and 67, the final products of Examples 69–83 (listed in tabular form) are derived.

C. and 1.0 ml. (0.02 mol) of bromine in 8 ml. of acetic acid is added dropwise. The reaction mixture is held at 60°–70° C. for one hour and then poured into ice. Toluene is added. The toluene layer is separated, washed

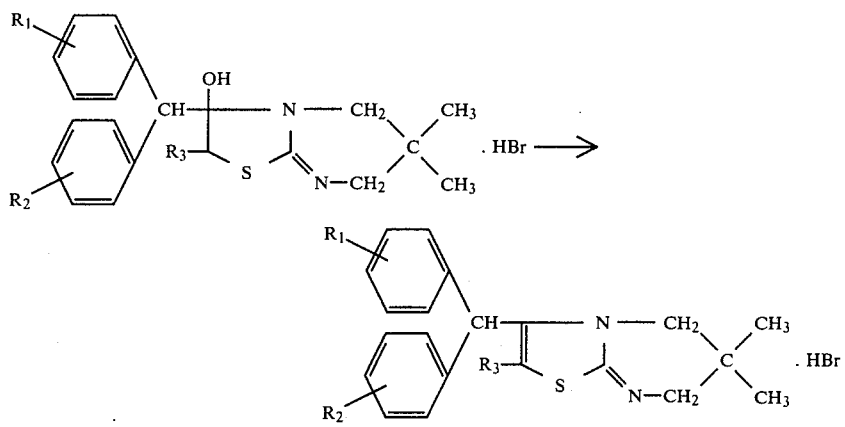

| Ex. | Starting Material Ex. No. | Product | Reaction Conditions Minutes | °C. | M.P. °C. |
|---|---|---|---|---|---|
| 69 | 51 | 3-diphenylmethyl-6,7-dihydro-6,6-dimethyl-5H-thiazolo[3,2-a]pyrimidine hydrobromide | 20 | 225 | 265–267 |
| 70 | 55 | 3-(p-methyl-α-phenylbenzyl)-6,7-dihydro-6,6-dimethyl-5H-thiazolo[3,2-a]pyrimidine hydrobromide | 30 | 190 | 262–265 |
| 71 | 54 | 3-(p-bromo-α-phenylbenzyl)-6,7-dihydro-6,6-dimethyl-5H-thiazolo[3,2-a]pyrimidine hydrobromide | 20 | 200 | 250–253 |
| 72 | 52 | 3-(p-chloro-α-phenylbenzyl)-6,7-dihydro-6,6-dimethyl-5H-thiazolo[3,2-a]pyrimidine hydrobromide | 20 | 200 | 268–270 |
| 73 | 57 | 3-(o-fluoro-α-p-tolylbenzyl)-6,7-dihydro-6,6-dimethyl-5H-thiazolo[3,2-a]pyrimidine hydrobromide | 20 | 200 | 263–266 |
| 74 | 58 | 3-(p-fluoro-α-p-tolylbenzyl)-6,7-dihydro-6,6-dimethyl-5H-thiazolo[3,2-a]pyrimidine hydrobromide | 20 | 200 | 257–260 |
| 75 | 56 | 3-(m-chloro-α-p-tolylbenzyl)-6,7-dihydro-6,6-dimethyl-5H-thiazolo[3,2-a]pyrimidine hydrobromide | 20 | 200 | 257–259 |
| 76 | 59 | 3-[p-chloro-α-(p-fluorophenyl)benzyl]-6,7-dihydro-6,6-dimethyl-5H-thiazolo[3,2-a]pyrimidine hydrobromide | 15 | 220 | 273–275 |
| 77 | 64 | 3-(p-fluoro-α-m-tolylbenzyl)-6,7-dihydro-6,6-dimethyl-5H-thiazolo[3,2-a]pyrimidine hydrobromide | 30 | 205–215 | 240–242 |
| 78 | 60 | 3-[o-chloro-α-(p-fluorophenyl)benzyl]-6,7-dihydro-6,6-dimethyl-5H-thiazolo[3,2-a]pyrimidine hydrobromide | 30 | 205–215 | 310–312 |
| 79 | 66 | 3-(p-fluoro-α-phenylbenzyl)-6,7-dihydro-2,6,6-trimethyl-5H-thiazolo[3,2-a]pyrimidine hydrobromide | 30 | 195–200 | 215–217 |
| 80 | 61 | 3-[o-fluoro-α-(p-fluorophenyl)benzyl]-6,7-dihydro-6,6-dimethyl-5H-thiazolo[3,2-a]pyrimidine hydrobromide | 30 | 210–230 | 293–295 |
| 81 | 62 | 3-[m-fluoro-α-(p-fluorophenyl)benzyl]-6,7-dihydro-6,6-dimethyl-5H-thiazolo[3,2-a]pyrimidine hydrobromide | 30 | 210–220 | 270–272 |
| 82 | 63 | 3-[bis-(p-fluorophenyl)methyl]-6,7-dihydro-6,6-dimethyl-5H-thiazolo[3,2-a]pyrimidine hydrobromide | 40 | 210 | 261–267 |
| 83 | 67 | 3-[bis-(p-fluorophenyl)methyl-6,7-dihydro-2,6,6-trimethyl-5H-thiazolo[3,2-a]pyrimidine hydrobromide | 20 | 195–200 | 215–217 |

EXAMPLE 84

3-Diphenylmethyl-2,3,5,6,7,8-hexahydrothiazolo[3,2-a][1,3]diazepin-3-ol hydrobromide A solution of 4.20 g. (0.02 mol) of 1,1-diphenyl-2-propanone in 25 ml. of acetic acid is heated at 60°--70° with water, dried over magnesium sulfate and concentrated to obtain 1-bromo-3,3-diphenyl-2-propanone.

The 1-bromo-3,3-diphenyl-2-propanone is dissolved in 30 ml. of acetone and added to a boiling mixture of 1.82 g. (0.14 mol) of hexahydro-2H-1,3-diazepine-2-thione in 100 ml. of acetone. This mixture is allowed to stand at room temperature for 24 hours, then the product is collected by filtration, washed with acetone and dried in vacuo at 50° C., giving the product as a solid, m.p. 194°-195° C. (dec.).

When the procedure of Example 84 is carried out using, instead of 1,1-diphenyl-2-propanone, the intermediate diarylketones of Examples 1-20, the final products of Examples 85-100 (listed in tabular form) are derived.

EXAMPLE 101

3-Diphenylmethyl-2,3,5,6,7,8-hexahydrothiazolo[3,2-a][1,3]diazepin-3-ol

A solution of 4.2 g. of 3-diphenylmethyl-2,3,5,6,7,8-hexahydrothiazolo[3,2-a][1,3]diazepin-3-ol hydrobromide in 50 ml. of 65% aqueous methanol is treated with 12 ml. of 1 N sodium hydroxide. The resulting solid is collected by filtration, washed with water and dried in

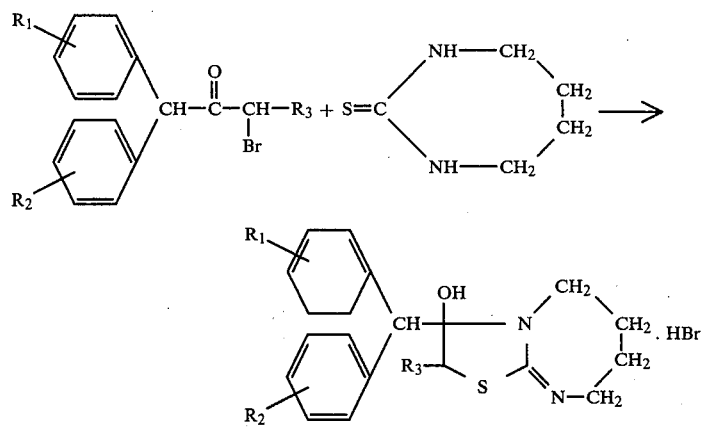

| Ex. | Intermediate Ex. No. | Product | M.P. °C. |
|---|---|---|---|
| 85 | 2 | 3-(p-chloro-α-phenylbenzyl-2,3,5,6,7,8-hexahydro-thiazolo[3,2-a][1,3]diazepin-3-ol hydrobromide | 202-204 |
| 86 | 3 | 3-(p-fluoro-α-phenylbenzyl)-2,3,5,6,7,8-hexahydro-thiazolo[3,2-a][1,3]diazepin-3-ol hydrobromide | 183-185 |
| 87 | 4 | 3-(p-bromo-α-phenylbenzyl)-2,3,5,6,7,8-hexahydro-thiazolo[3,2-a][1,3]diazepin-3-ol hydrobromide | 169-171 |
| 88 | 5 | 3-(p-methyl-α-phenylbenzyl)-2,3,5,6,7,8-hexahydro-thiazolo[3,2-a][1,3]diazepin-3-ol hydrobromide | 198-200 |
| 89 | 7 | 3-(o-fluoro-α-p-tolylbenzyl)-2,3,5,6,7,8-hexa-hydrothiazolo[3,2-a][1,3]diazepin-3-ol hydrobromide | 176-178 |
| 90 | 9 | 3-(p-fluoro-α-p-tolylbenzyl)-2,3,5,6,7,8-hexa-hydrothiazolo[3,2-a][1,3]diazepin-3-ol hydrobromide | 184-186 |
| 91 | 10 | 3-(m-methyl-α-p-tolylbenzyl)2,3,5,6,7,8-hexahydro-thiazolo[3,2-a][1,3]diazepin-3-ol hydrobromide | 191-193 |
| 92 | 12 | 3-[p-chloro-α-(p-fluorophenyl)benzyl]-2,3,5,6,7,8-hexahydrothiazolo[3,2-a][1,3]diazepin-3-ol hydrobromide | 197-199 |
| 93 | 13 | 3-[o-chloro-α-(p-fluorophenyl)benzyl]-2,3,5,6,7,8-hexahydrothiazolo[3,2-a][1,3]diazepin-3-ol hydrobromide | 175-177 |
| 94 | 14 | 3-[o-fluoro-α-(p-fluorophenyl)benzyl]-2,3,5,6,7,8-hexahydrothiazolo[3,2-a][1,3]diazepin-3-ol hydrobromide | 204-206 |
| 95 | 15 | 3-[m-fluoro-α-(p-fluorophenyl)benzyl]-2,3,5,6,7,8-hexahydrothiazolo[3,2-a][1,3]diazepin-3-ol hydrobromide | 189-191 |
| 96 | 16 | 3-[bis(p-fluorophenyl)methyl]-2,3,5,6,7,8-hexa-hydrothiazolo[3,2-a][1,3]diazepin-3-ol hydrobromide | 187-189 |
| 97 | 17 | 3-(p-fluoro-α-m-tolylbenzyl)-2,3,5,6,7,8-hexa-hydrothiazolo[3,2-a][1,3]diazepin-3-ol hydrobromide | 180-182 |
| 98 | 18 | 3-(p-chloro-α-phenylbenzyl)-2,3,5,6,7,8-hexahydro-2-methylthiazolo[3,2-a][1,3]diazepin-3-ol hydrobromide | 187-189 |
| 99 | 19 | 3-(p-fluoro-α-phenylbenzyl)-2,3,5,6,7,8-hexahydro-2-methylthiazolo[3,2-a][1,3]diazepin-3-ol hydrobromide | 198-200 |
| 100 | 20 | 3-[bis(p-fluorophenyl)methyl]-2,3,5,6,7,8-hexa-hydro-2-methylthiazolo[3,2-a][1,3]diazepin-3-ol hydrobromide | 182-189 | vacuo at 40° C., giving the desired product, m.p. 123°—125° C.

93-96 and 100, the final products of Examples 104-111 (listed in tabular form) are derived.

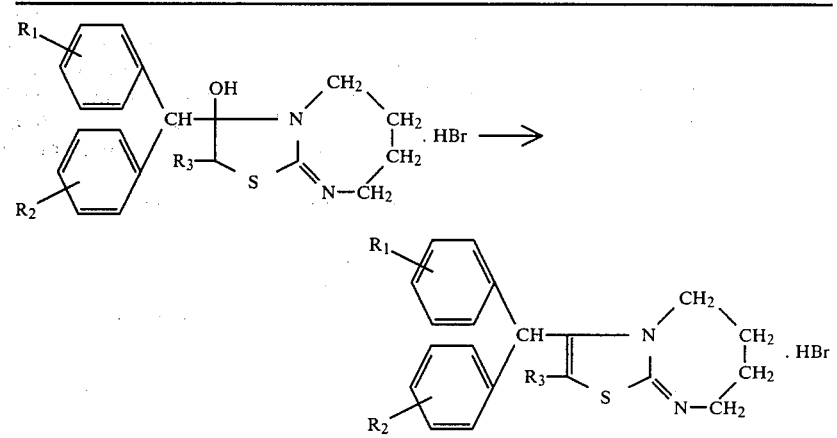

| Ex. | Starting Material Ex. No. | Product | Reaction Conditions Minutes | °C. | M.P. °C. |
|---|---|---|---|---|---|
| 104 | 84 | 3-diphenylmethyl-5,6,7,8-tetrahydrothiazolo-[3,2-a][1,3]diazepine hydrobromide | 20 | 200 | 260-262 |
| 105 | 86 | 3-(p-fluoro-α-phenylbenzyl)-5,6,7,8-tetrahydrothiazolo[3,2-a][1,3]diazepine hydrobromide | 10 | 195 | 210-212 |
| 106 | 89 | 3-(o-fluoro-α-p-tolylbenzyl)-5,6,7,8-tetrahydrothiazolo[3,2-a][1,3]diazepine hydrobromide | 10 | 210 | 212-215 |
| 107 | 93 | 3-[o-chloro-α-(p-fluorophenyl)benzyl]-5,6,7,8-tetrahydrothiazolo[3,2-a][1,3]diazepine hydrobromide | 25 | 190-200 | 243-245 |
| 108 | 94 | 3-[o-fluoro-α-(p-fluorophenyl)benzyl]-5,6,7,8-tetrahydrothiazolo[3,2-a][1,3]diazepine hydrobromide | 20 | 210-215 | 208-210 |
| 109 | 95 | 3-[m-fluoro-α-(p-fluorophenyl)benzyl]-5,6,7,8-tetrahydrothiazolo[3,2-a][1,3]diazepine hydrobromide | 15 | 195-200 | 220-222 |
| 110 | 96 | 3-[bis-(p-fluorophenyl)methyl]-5,6,7,8-tetrahydrothiazolo[3,2-a][1,3]diazepine hydrobromide | 15 | 210 | 239-242 |
| 111 | 100 | 3-[bis-(p-fluorophenyl)methyl]-5,6,7,8-tetrahydro-2-methylthiazolo[3,2-a][1,3]diazepine hydrobromide | 20 | 190 | 277-280 |

EXAMPLE 102

3-Diphenylmethyl-2,3,5,6,7,8-hexahydrothiazolo[3,2-a][1,3]diazepin-3-ol hydrochloride A solution of 3.0 g. of 3-diphenylmethyl-2,3,5,6,7,8-hexahydrothiazolo[3,2-a][1,3]diazepin-3-ol in 30 ml. of acetone is treated with 4 ml. of 3 N ethanolic hydrochloric acid. The resulting solid is collected by filtration, giving the desired product, m.p. 205° C. (dec.).

EXAMPLE 103

3-[p-Chloro-α-(p-fluorophenyl)benzyl]-5,6,7,8-tetrahydrothiazolo[3,2-a][1,3-diazepine, hydrobromide A flask containing 2.0 g. of 3-[p-chloro-α-(p-fluorophenyl)benzyl]-2,3,5,6,7,8,-hexahydrothiazolo[3,2-a][1,3]diazepin-3-ol hydrobromide is immersed in an oil bath at 210° C. and left for 20 minutes. The flask is removed the reaction mixture is triturated with acetone, filtered and washed with acetone, giving the desired product, m.p. 239°-241° C.

When the procedure of Example 103 is carried out using, instead of 3-[p-chloro-α-(p-fluorophenyl)benzyl]-2,3,5,6,7,8-hexahydrothiazolo[3,2-a][1,3]diazepin-3-ol hydrobromide, the compounds of Examples 84, 86, 89,

EXAMPLE 112

3-Diphenylmethyl-2,3,6,7,8-hexahydro-5H-thiazolo[3,2-a][1,3]diazocin-3-ol hydrobromide 1-Bromo-3,3-diphenyl-2-propanone is reacted with hexahydro-1,3-diazocine-2(1H)-thione by the procedure of Example 84, giving the desired product, m.p. 211°-213° C. (dec.).

EXAMPLE 113

3-Diphenylmethyl-6,7,8,9-tetrahydro-5H-thiazolo[3,2-a][1,3]diazocine hydrobromide A test tube containing 1.0 g. of 3-diphenylmethyl-2,3,6,7,8,9-hexahydro-5H-thiazolo[3,2-a][1,3]diazocin-3-ol hydrobromide is immersed in an oil bath at 215° C. for 20 minutes. The tube is then removed, acetone is added and the product is collected by filtration, m.p. 250°-252° C.

EXAMPLE 114

3-(p-Fluoro-α-phenylbenzyl)-6,7-dihydro-2,6,6-trimethyl-5H-thiazolo[3,2-a]pyrimidine hydrobromide One gram of 3-(p-fluoro-α-phenylbenzyl)-2,3,6,7,-tetrahydro-2,6,6-trimethyl-5H-thiazolo[3,2-a]pyrimidin-3-ol hydrobromide is immersed in an oil bath at 190° C. for 20 minutes. The reaction mixture is triturated with acetone and the desired product is recovered by filtration.

EXAMPLE 115

3-(p-Chloro-α-phenylbenzyl)-5,6,7,8-tetrahydro-2-methylthiazolo[3,2-a][1,3]diazepine hydrobromide A 1.0 g. of 3-(p-chloro-α-phenylbenzyl)-2,3,5,6,7,8-hexahydro-2-methylthiazolo[3,2-a][1,3]diazepin-3-ol hydrobromide is placed in a flask and immersed in an oil bath at 200° C. for 20 minutes giving the desired product.

We claim:

1. A compound selected from the group consisting of those of the formula:

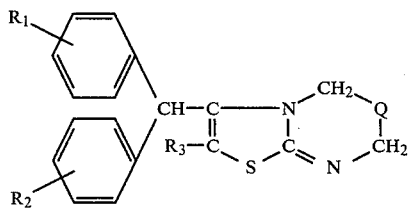

wherein $R_1$ and $R_2$ may be the same or different and are hydrogen, fluoro, chloro, bromo or alkyl having up to 3 carbon atoms; $R_3$ is hydrogen or alkyl having up to 3 carbon atoms; and Q is a divalent moiety of the formula:

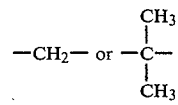

and the pharmacologically acceptable acid-addition salts thereof.

2. The compound according to claim 1 wherein $R_1$ is ortho-fluoro, $R_2$ is para-fluoro, $R_3$ is hydrogen and Q is —CH$_2$—; 3-[o-fluoro-α-(p-fluorophenyl)benzyl]-6,7-dihydro-5H-thiazolo[3,2-a]pyrimidine.

3. The compound according to claim 1 wherein $R_1$ is para-chloro, $R_2$ is para-fluoro, $R_3$ is hydrogen and Q is —CH$_2$—; 3-[p-chloro-α-(p-fluorophenyl)benzyl]-6,7-dihydro-5H-thiazolo[3,2-a]pyrimidine.

4. The compound according to claim 1 wherein $R_1$ and $R_2$ are both para-fluoro, $R_3$ is hydrogen and Q is —CH$_2$—; 3-[bis-(p-fluorophenyl)methyl]-6,7-dihydro-5H-thiazolo[3,2-a]pyrimidine.

5. The compound according to claim 1 wherein $R_1$ is para-fluoro, $R_2$ and $R_3$ are both hydrogen and Q is —C(CH$_3$)$_2$—; 3-(p-fluoro-α-phenylbenzyl)-6,7-dihydro-6,6-dimethyl-5H-thiazolo[3,2-a]pyrimidine.

6. The compound according to claim 1 wherein $R_1$ is ortho-chloro, $R_2$ is para-fluoro, $R_3$ is hydrogen and Q is —C(CH$_3$)$_2$—; 3-[o-chloro-α-(p-fluorophenyl)benzyl]-6,7-dihydro-6,6-dimethyl-5H-thiazolo[3,2-a]pyrimidine.

7. The compound according to claim 1 wherein $R_1$ is para-chloro, $R_2$ is para-fluoro, $R_3$ is hydrogen and Q is —C(CH$_3$)$_2$—; 3-[p-chloro-α-(p-fluorophenyl)benzyl]-6,7-dihydro-6,6-dimethyl-5H-thiazolo[3,2-a]pyrimidine.

8. The compound according to claim 1 wherein $R_1$ is ortho-fluoro, $R_2$ is para-fluoro, $R_3$ is hydrogen and Q is —C(CH$_3$)$_2$—; 3-[o-fluoro-α-(p-fluorophenyl)benzyl]-6,7-dihydro-6,6-dimethyl-5H-thiazolo[3,2-a]pyrimidine.

9. The compound according to claim 1 wherein $R_1$ and $R_2$ are both para-fluoro, $R_3$ is hydrogen and Q is —C(CH$_3$)$_2$—; 3-[bis-(p-fluorophenyl)methyl]-6,7-dihydro-6,6-dimethyl-5H-thiazolo[3,2-a]pyrimidine.

10. The method of promoting diuresis in a mammal which comprises administering to said mammal an effective diuretic amount of a compound of claim 1.

11. A diuretic composition of matter in dosage unit form comprising from about one mg. to about 500 mg. of a compound of claim 1 in association with a pharmaceutical carrier.

* * * * *